US00PP27649P2

(12) United States Plant Patent
van Zoest

(10) Patent No.: US PP27,649 P2
(45) Date of Patent: Feb. 7, 2017

(54) ***CLEMATIS* PLANT NAMED 'ZO09045'**

(50) Latin Name: ***Clematis* hybrid**
Varietal Denomination: Zo09045

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 117 days.

(21) Appl. No.: 14/544,322

(22) Filed: Dec. 23, 2014

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Appleby. Horticulture Week. Plantarium releases details of plants entered for the show's new plant awards, 2014, retrieved on Jun. 7, 2016, retrieved from the Internet at <http://www.hortweek.com/plantarium-releases-details-plants-entered-shows-new-plant-awards/ornamentals/article/1307554> 12 pp.*

* cited by examiner

*Primary Examiner* — June Hwu
(74) *Attorney, Agent, or Firm* — Penny J. Aguirre

(57) ABSTRACT

A new cultivar of hybrid *Clematis*, 'Zo09045' that is characterized by its mostly upright facing flowers with upright facing tepals, its abundance of flowers, its purple flowers that retain their color with very little fading, its sterility, and its cold hardiness to at least U.S.D.A. Zone 5.

2 Drawing Sheets

Botanical classification: *Clematis* hybrid.
Variety denomination: 'Zo09045'.

BACKGROUND OF THE INVENTION

The present invention relates to a new and distinct cultivar of *Clematis* of hybrid origin (Diversifolia Group) and will be referred to hereafter by its cultivar name 'Zo09045'. *Clematis* 'Zo09045' is grown as an herbaceous perennial for landscape use, as a flowering potted plant for the terrace and as a cut flower.

*Clematis* 'Zo09045' derived from an ongoing breeding program by the Inventor at his nursery in Boskoop, The Netherlands. The goal of the selection was to select a hardy herbaceous perennial with uniquely colored flowers that is easy to grow and propagate and that could be grown for different purposes. *Clematis* 'Zo09045' was selected in 2009 and arose from a controlled cross made in 2006 between unnamed and unpatented plants from his breeding program; the female parent designated as No. 20040222 and the male parent designated as No. 20030033.

Asexual propagation of the new cultivar was first accomplished by internodial stem cuttings under the direction of the Inventor in Boskoop, The Netherlands in 2009. Asexual propagation by internodial stem cutting has determined that the characteristics of the new cultivar are stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish *Clematis* 'Zo09045' as a unique cultivar of *Clematis*.

1. 'Zo09045' exhibits mostly upright facing flowers.
2. 'Zo09045' exhibits upright facing tepals.
3. 'Zo09045' exhibits flowers that are deep purple in color and retain their color with very little fading.
4. 'Zo09045' is sterile and no seed is produced.
5. 'Zo09045' is cold hardy to at least U.S.D.A. Zone 5.

'Zo09045' differs from its female parent in having flowers that are mostly upright while the female parent has nodding flowers. 'Zo09045' differs from its male parent in having upright facing tepals while the male parent has spreading tepals. 'Zo09045' can be most closely compared to the cultivars 'Durandii' (not patented) and 'Zo06137' (U.S. Plant Pat. No. 25,898) and the differences are described in TABLE 1.

TABLE 1

| *Clematis* cultivar | Characteristic | Description | 'Zo09045' |
|---|---|---|---|
| 'Durandii' | Flower size | 7-14 cm in diameter | 4-6 cm in diameter |
| 'Durandii' | Tepal aspect | Fully spreading | Upright |
| 'Durandii' | Connective color | Yellow | Dark purple |
| 'Zo06137' | Tepal aspect | Almost spreading | Upright |
| 'Zo06137' | Stamen shape | Straight | Bent at upper half |
| 'Zo06137' | Connective color | Yellow | Dark purple |

BRIEF DESCRIPTION OF THE DRAWINGS

The accompanying colored photographs illustrate the overall appearance and distinct characteristics of the new *Clematis*. The photographs were taken of a three year-old plant of 'Zo09045' as grown in a 5-gallon container (FIG. 1) or in a 1-gallon container (FIG. 2, FIG. 3, FIG. 4) in Boskoop, The Netherlands.

The photograph in FIG. 1 shows the habitus and leaves.

Figure 1:
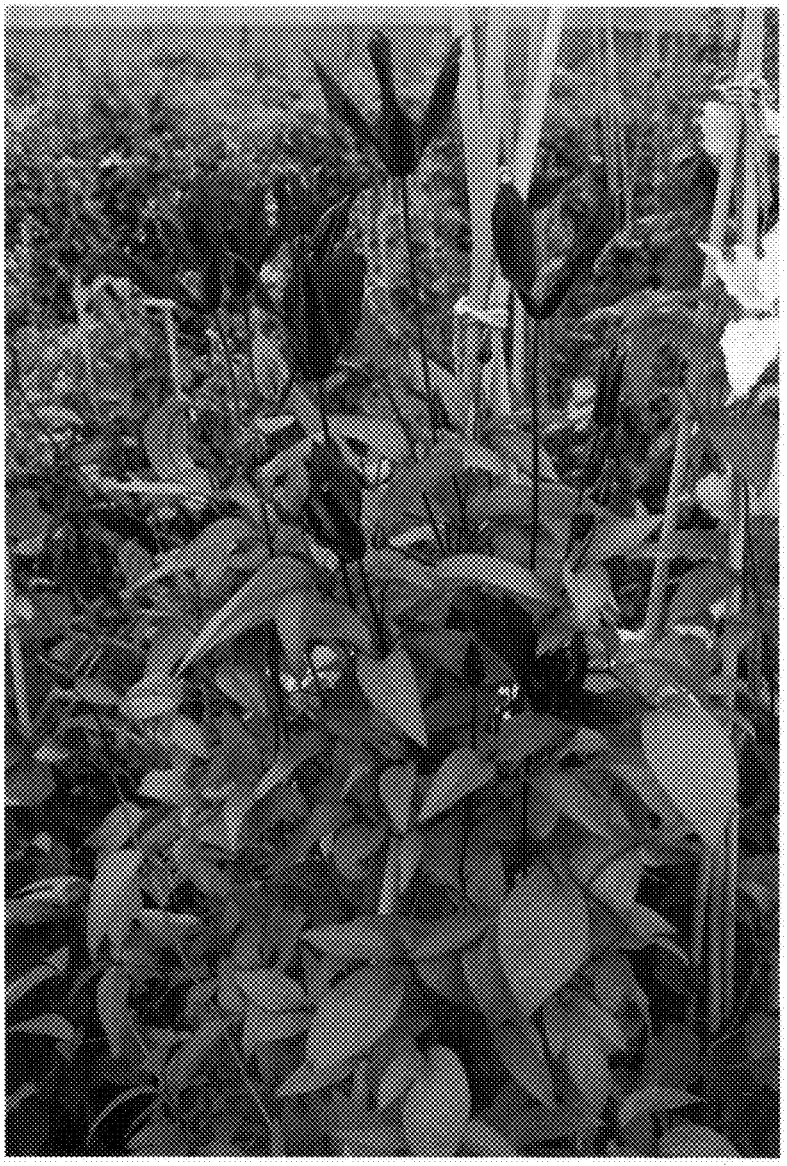
Figure 2:
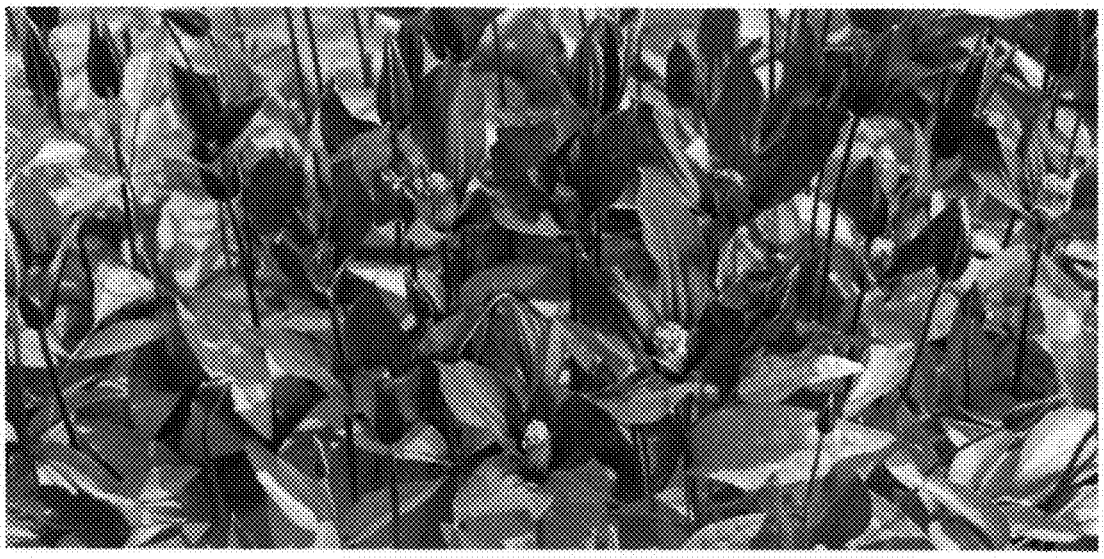

The photograph in FIG. 2 shows the flowers.

Figure 3:
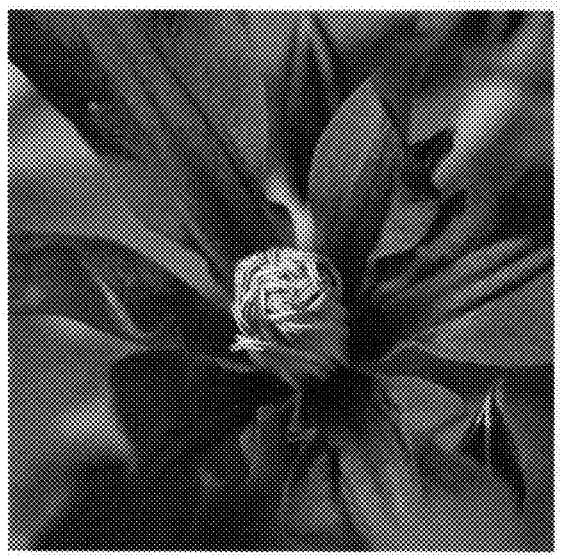

The photograph in FIG. 3 shows the inside of the flower with a close up of the stamens.

Figure 4:
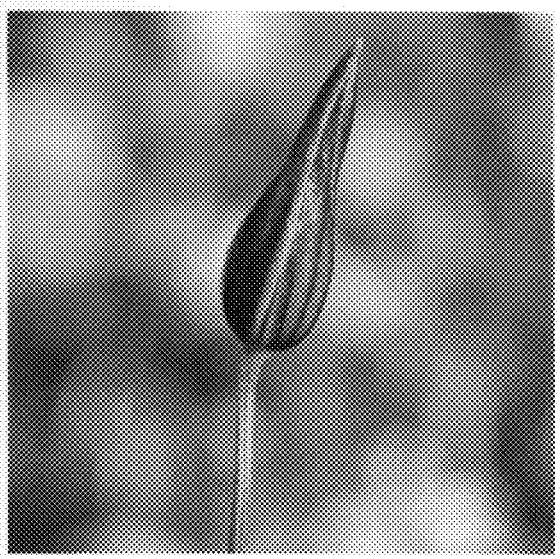

The photograph in FIG. 4 shows the flower bud.

The colors of the photographs are as close as possible with the digital photography techniques available and the color values cited in the detailed botanical description accurately describe the colors of the new *Clematis*.

DETAILED BOTANICAL DESCRIPTION

The following is a detailed description of three year-old plants of 'Zo09045' as grown outdoors in full sun in one-gallon containers at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Colour Chart, London, England, except where general color terms of ordinary dictionary significance are used.

General description:

*Botanical classification.*—*Clematis* 'Zo09045' (classified in the Diversifolia Group).

*Blooming period.*—From late spring to late summer on current year's growth.

*Plant type.*—Herbaceous perennial.

*Plant habit.*—Bushy, semi-upright.

*Height and spread.*—Three year-old plant is about 20 cm in width at the base and up to 1 m in height when pruned hard in late winter.

*Cold hardiness.*—At least to U.S.D.A. Zone 5.

*Culture.*—Moist but well-drained soils in full sun with the roots shaded.

*Diseases and pests.*—Susceptibility to powdery mildew caused by *Erysiphe polygoni* is unknown, no pest problems have been observed.

*Root description.*—Fleshy.

Growth and propagation:

*Propagation.*—Internodial soft wood cuttings from vegetative shoots.

*Root initiation.*—Roots develop in 5 weeks in summer under greenhouse conditions.

*Time required for root development.*—75 to 90 days to develop a 7-cm container from a 5-cm cutting.

*Growth rate.*—Vigorous and very free flowering but tidy once planted in the landscape.

Stem description:

*Shape.*—Round and 6-ribbed.

*Stem color.*—166B in color and ribbed 166A.

*Stem size.*—From about 0.5 to 1 m in length (including peduncle and terminal pedicel), an average of 1 to 3 mm in diameter.

*Stem surface.*—Sparsely covered with hairs.

*Internode length.*—2 to 6 cm long.

*Branching.*—Branching from the base.

Foliage description:

*Leaf arrangement.*—Opposite.

*Leaf division.*—Simple or ternate.

*Leaf size.*—Up to 9 cm in length and an average of 4.5 cm in width.

*Leaf attachment.*—Petiolate.

*Leaf shape.*—Small elliptic to lanceolate.

*Leaf base.*—Cuneate at terminal leaflet, oblique at side leaflets.

*Leaf apex.*—Acute to acuminate.

*Leaf fragrance.*—Clearly a "sharp" fragrance when crushed.

*Leaf venation.*—Upper surface slightly reticulate, lower surface less reticulate, primarily matches leaf color on both surfaces and main veins on lower surface can be flushed with 59A.

*Leaf margin.*—Entire with simple leaves sometimes lobed.

*Leaf surface.*—Upper surface; glabrous, lower surface; glabrous with a few sparse hairs at the margin.

*Leaf color.*—Upper surface; 137B, lower surface; 147C.

*Petioles.*—1 to 4 cm in length, 1 mm in diameter, 146C flushed 59A in color, round and caniculate above, surface glabrous with a few hairs.

*Petiolules.*—1 to 3 cm in length, 146C flushed 59A in color, surface is primarily glabrous with a few hairs.

Inflorescence description:

*Inflorescence type.*—Solitary or a few flowered dichasial cyme.

*Inflorescence arrangement.*—Terminal and axillary on young shoots.

*Peduncles.*—Up to 7 cm in length and an average of 4 mm in width, 137B in color, round, surface slightly 6 ribbed and sparsely short hairy.

*Pedicels.*—Up to 9 cm in length and an average of 4 mm in width, 137B in color and ribbed with N92C, round in shape, surface slightly ribbed and covered with short hairs, more densely towards the base of the tepals.

*Flower buds.*—Mostly upright with a slightly nodding stage, lanceolate in shape, apex acuminate, an average of 5 cm in length and 2 cm in width, base obtuse, 79A in color, surface glabrous with sparsely villous seams.

*Flower fragrance.*—Not fragrant.

*Lastingness of the flowers.*—Individual flowers last up to about 6 to 8 days until the first tepal drops, followed later by the stamens.

*Flower quantity.*—Solitary or up to 5 to 9 per stem.

*Flower type.*—Single, campanulate.

*Flower aspect.*—Mostly upright.

*Flower size.*—5 to 6 cm in diameter, up to 8 cm in depth.

*Flower sex.*—Bisexual.

*Tepal number.*—4.

*Tepal shape.*—Small elliptic to oblanceolate, squeezed or flat.

*Tepal apex.*—Acuminate.

*Tepal base.*—Cuneate.

*Tepal margin.*—Entire and moderately undulate.

*Tepal surface.*—Inner surface; glabrous, outer surface; glabrous with villous margin.

*Tepal color.*—Inner surface; N92B flushed N92A at margin at the apex, outer surface; 95A with 93A ribs, margin with grey hairs.

*Tepal size.*—Up to 8 cm in length and 2.5 cm in width.

Reproductive organs:

*Gynoecium.*—Average of 20 to 30 pistils, up to 1.4 cm in length, ovary 143C in color with short hairs on surface, style 161D in color and plumose, stigma white in color and slightly bent.

*Androcoecium*.—An average of 60 stamen per flower, filaments are 0.5 to 1.6 cm in length, 0.1 cm in width and linear in shape, surface is glabrous but sparsely hairy below the anthers, color of outer filaments are N89C at the base, about 155A in middle, and N87D towards anthers, anthers are 0.4 cm in length and 1 mm in width, linear in shape, and 155C in color; connective is very short elongated, apex acute, surface glabrous and N79B in color.

*Seed*.—Seed is not formed, observed to be sterile.

It is claimed:

1. A new and distinct cultivar of *Clematis* plant named 'Zo09045' as herein illustrated and described.

* * * * *